United States Patent [19]

Bourdon

[11] Patent Number: 4,674,318
[45] Date of Patent: Jun. 23, 1987

[54] APPARATUS FOR THE MEASUREMENT OF THE RESISTANCE TO SHOCK

[75] Inventor: Raymond Bourdon, Moneim, France

[73] Assignee: Atochem, France

[21] Appl. No.: 809,735

[22] Filed: Dec. 17, 1985

[30] Foreign Application Priority Data

Jan. 14, 1985 [FR] France .................. 85 00426

[51] Int. Cl.[4] ............................................. G01N 3/30
[52] U.S. Cl. .......................................... 73/12; 374/46
[58] Field of Search .............. 73/12, 82, 87, 838, 73/839; 374/46, 52, 53

[56] References Cited

U.S. PATENT DOCUMENTS

| 2,748,596 | 6/1956 | Tasker ........................... 73/12 |
| 2,892,342 | 6/1959 | Goss et al. ..................... 73/12 |
| 3,056,279 | 10/1962 | Milewski et al. ............. 73/12 X |

FOREIGN PATENT DOCUMENTS

| 666058 | 2/1952 | United Kingdom ............ 73/12 |
| 1104953 | 3/1968 | United Kingdom ............ 73/12 |

Primary Examiner—Charles A. Ruehl
Attorney, Agent, or Firm—Sigalos & Levine

[57] ABSTRACT

An apparatus for the measurement of the resistance of a test-piece to shock comprising an anvil, a mass positioned for movement along said axis and into contact with said test-piece positioned at said opening, and a movable thermal medium having a male part with a surface which is penetrable into said opening of said anvil sufficiently for conducting heat to or from said test-piece to bring it to a specified temperature and which is retractable from said opening as said mass moves to contact said test-piece.

20 Claims, 1 Drawing Figure

4,674,318

APPARATUS FOR THE MEASUREMENT OF THE RESISTANCE TO SHOCK

BACKGROUND OF THE INVENTION

The present invention pertains to an apparatus for the measurement of the resistance to shock and more particularly to a system and apparatus used therewith for bringing the test-pieces to a testing temperature and for testing the resistance to shock of the test-pieces at such testing temperature.

Basically, apparatuses for the measurement of the resistance to shock, for example, such apparatuses which are useful for the quality control of plastic materials, essentially include an anvil, which is hollow along an axis of the fall of the mass. In some shock testing apparatuses bits may be provided for fastening the test-piece to the anvil. Means for the measuring and recording of the test results will be provided but these means are beyond the scope of the present invention.

In the case of cold measurements, according to prior art, the test-piece is cooled by placing it along with the anvil and the fixation bits in a cooled enclosure. When the test-piece has reached the desired temperature, the entire unit is removed from the enclosure so that the test-piece may be immediately subjected to shock. Such a system necessitates much cooling-down preparation; moreover, the method is slow and costly. Thus, such systems are particularly disadvantageous because of the loss of time for the cooling the entire fixation unit along with the test-piece. Also, energy loss for the same cooling down is costly.

SUMMARY OF THE INVENTION

The present invention consists of a preparation which permits cooling of the test-piece alone.

Briefly, one introduces a thermal medium through an opening in the anvil or through a hollow part of the anvil and into contact with the test-piece. When the test-piece reaches the proper temperature, the thermal medium is removed and a moving mass comes into contact with the test-piece. The removal of the thermal medium and contact by the mass occur substantially simultaneously, due to the arrangement of a control means. Taking into account the mobility of the thermal medium, the apparatus is not exclusively reserved for the measurements of shock to cold.

An apparatus for the measurement of the resistance of a test-piece to shock comprises an anvil, a mass positioned for movement along the axis of said anvil and into contact with said test-piece positioned at the anvil opening, and a movable thermal medium having a male part with a surface which is penetrable into said opening of said anvil sufficiently for conducting heat to or from said test-piece to bring said test piece to a specified temperature and which thermal medium male part is retractable from said opening as said mass moves to contact said test-piece.

DETAILED DESCRIPTION

Figure 1:
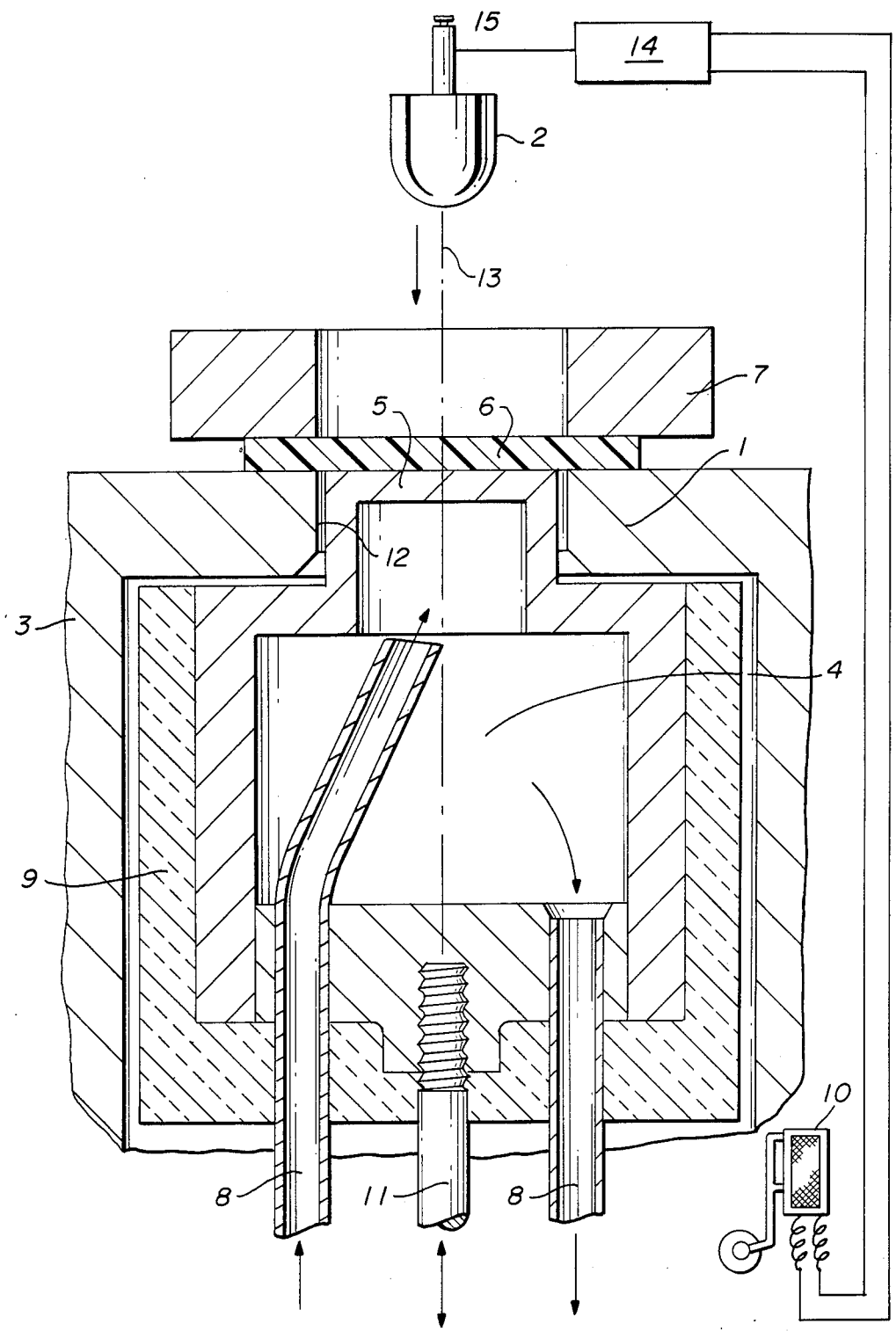
FIG. 1 is a sectional view of an embodiment of the apparatus for the measurement of resistance to shock.

The enclosed FIG. 1 illustrates the description of the apparatus. The apparatus consists of an anvil 1 having an opening 12 pierced through said anvil along an axis 13 corresponding to the axis 13 of the fall of a mass 2 and preferably said anvil is fixed on a support 3. A thermal medium 4 is characterized in that the thermal medium 4 is independent of the anvil 1 and movable by means 11, said thermal medium 4 has a male part 5. In a preferred embodiment, the perimeter of said male part substantially corresponds to the perimeter of the opening in the anvil when said male part is inserted into the female part of the anvil (i.e., into the opening). A surface of said male part is penetrable into said opening sufficiently for conducting heat to or from said test-piece. Preferably, said surface contacts said test-piece as by coming to the minimum perpendicular to the anvil surface on which the test-piece is positioned in order to come into contact with the test-piece 6 during the thermal exchange phase. Bits 7 may be provided to immobilize the test-piece onto the anvil. The thermal medium 4 is preferably a container in which, for example, a liquid is circulated by means of pipes 8 or which contains a medium allowing thermal exchange. In the case where one wishes to reheat the test-piece, an electrical resistance heating element may be placed in the male part 5. Depending upon various cost considerations, it may also be desirable to insulate at 9 the thermal medium 4.

One inventive aspect of the apparatus is found in the mobility of the thermal medium 4. When the test-piece is at the desired temperature, the thermal medium is retracted from the opening while releasing the mass 2 onto the test-piece. Certainly, the accuracy of the measurement lies within the deviation of the minimum time which must exist between the instant of breaking thermal contact between the test-piece and the thermal medium and the instant of impact of the mass with the test-piece. An efficient means of limiting this deviation of time consists of controlling the discharge or release of the mass 2 corresponding to the retraction or release of the thermal medium 4. This control means 10, 14, and 15 may consist of the movement of the thermal medium causing the engagement of a contact 10 situated along the path of retracted thermal medium which activates a discharge system 14 or releases the mass at 15.

A specific example, not intended to limit the invention, illustrates the invention. It is possible to raise the thermal medium onto a hydraulic system, such as a hydraulic jack. When the piston 11 of the jack discharges, the thermal medium retracts or falls abruptly; in the length of the fall the thermal medium meets the contact 10 which releases at 15 the discharge of the mass 2. The contact 10 may be, for example, a switch controlling an electromagnet system 14 or even a pneumatic system 14.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. An apparatus for the measurement of the resistance of a test-piece to shock comprising an anvil having an opening along an axis therethrough, a mass positioned for movement along said axis and into contact with said test-piece positioned at said opening, and a movable thermal medium having a male part with a surface which is penetrable into said opening of said anvil sufficiently for conducting heat to or from said test-piece to bring it to a specified temperature and which is retractable from said opening as said mass moves to contact said test-piece.

2. An apparatus according to claim 1, characterized in that the perimeter of the male part substantially corresponds to that of said opening through said anvil.

3. An apparatus according to claim 2, characterized in that said thermal medium is a reservoir containing a means for allowing thermal exchange.

4. An apparatus according to claim 3, further comprising means controlled by the movement of said thermal medium for causing movement of said mass.

5. An apparatus according to claim 4, wherein said means for causing movement of said mass comprises a contact engaged by the movement of said thermal medium which releases said mass to fall onto said test-piece.

6. An apparatus according to claim 5, wherein said means for causing movement of said mass further comprises a pneumatic system activated by engagement of said contact.

7. An apparatus according to claim 4, wherein said means for causing movement of said mass comprises a pneumatic system activated by movement of said thermal medium.

8. An apparatus according to claim 2, further comprising means controlled by the movement of said thermal medium for causing movement of said mass.

9. An apparatus according to claim 8, wherein said means for causing movement of said mass comprises a contact engaged by the movement of said thermal medium which releases said mass to fall onto said test-piece.

10. An apparatus according to claim 9, wherein said means for causing movement of said mass further comprises a pneumatic system activated by engagement of said contact.

11. An apparatus according to claim 8, wherein said means for causing movement of said mass comprises a pneumatic system activated by movement of said thermal medium.

12. An apparatus according to claim 1, characterized in that the thermal medium is a reservoir containing a means for allowing a thermal exchange.

13. An apparatus according to claim 12, further comprising means controlled by the movement of said thermal medium for causing movement of said mass.

14. An apparatus according to claim 13, wherein said means for causing movement of said mass for movement comprises a contact engaged by the movement of said thermal medium which releases said mass to fall onto said test-piece.

15. An apparatus according to claim 14, wherein said means for causing movement of said mass further comprises a pneumatic system activated by engagement of said contact.

16. An apparatus according to claim 13, wherein said means for causing movement of said mass comprises a pneumatic system activated by movement of said thermal medium.

17. An apparatus according to claim 1, further comprising means controlled by the movement of said thermal medium for causing movement of said mass.

18. An apparatus according to claim 17, wherein said means for causing movement of said mass comprises a contact engaged by the movement of said thermal medium which releases said mass to fall onto said test-piece.

19. An apparatus according to claim 18, wherein said means for causing movement of said mass further comprises a pneumatic system activated by engagement of said contact.

20. An apparatus according to claim 17, wherein said means for causing movement of said mass comprises a pneumatic system activated by movement of said thermal medium.

* * * * *